United States Patent [19]

Howland et al.

[11] Patent Number: 4,653,481

[45] Date of Patent: Mar. 31, 1987

[54] ADVANCED SPINE FIXATION SYSTEM AND METHOD

[76] Inventors: Robert S. Howland, 11730 Seaboard Cir., Stanton, Calif. 90680; Leon L. Wiltse, 2888 Long Beach Blvd., Long Beach, Calif. 90806

[21] Appl. No.: 873,611

[22] Filed: Jun. 18, 1986

Related U.S. Application Data

[63] Continuation-in-part of Ser. No. 758,294, Jul. 24, 1985.

[51] Int. Cl.$^4$ .............................................. A61B 17/56
[52] U.S. Cl. .................................. 128/69; 128/92 YM; 248/67.5; 248/68.1; 248/74.4
[58] Field of Search .................... 128/68, 69, 78, 84 R, 128/92 YM; 256/54, 55; 248/74.4, 68.1, 67.5

[56] References Cited

U.S. PATENT DOCUMENTS

| | | | |
|---|---|---|---|
| 3,693,616 | 9/1972 | Roaf et al. | 128/92 YM X |
| 4,041,939 | 8/1977 | Hall | 128/78 X |
| 4,078,559 | 3/1978 | Nissinen | 128/78 X |
| 4,085,744 | 4/1978 | Lewis et al. | 128/78 X |
| 4,131,257 | 12/1978 | Sterling | 248/67.5 |
| 4,273,465 | 6/1981 | Schoen | 248/67.5 X |
| 4,289,123 | 9/1981 | Dunn | 128/84 R |
| 4,409,968 | 10/1983 | Drummond | 128/69 |

Primary Examiner—Edgar S. Burr
Assistant Examiner—Moshe I. Cohen
Attorney, Agent, or Firm—Beehler, Pavitt, Siegemund, Jagger, Martella & Dawes

[57] ABSTRACT

An advanced spine fixation system includes a plurality of screw clamp assemblies preferably inserted through the pedicle and vertebral body at the vertebra. Each screw clamp includes a removable saddle assembly composed of two halves and each provided with apertures for the reception of rigid support rods which, in one form, form a parallelogram. In another form, the screw clamp receives a single rod, the clamp apertures and the rod being serrated for increasing the purchase. The apertures are proportioned to provide an interference fit with the rods to effect purchase between the saddles and the rods. In use, the screws and clamps are properly placed and a soft temporary master is formed which follows and replicates the contour of reference surfaces on the clamps. The temporary master is then used to form a master pattern which in turn is used to form the rigid rods to the determined contour. The rigid rods are then affixed to the clamp assemblies to provide the rigid support needed for spinal procedures. Details of the system and method are set forth.

25 Claims, 27 Drawing Figures

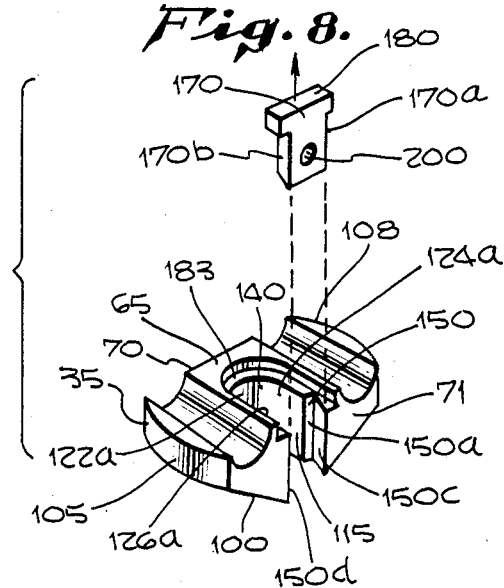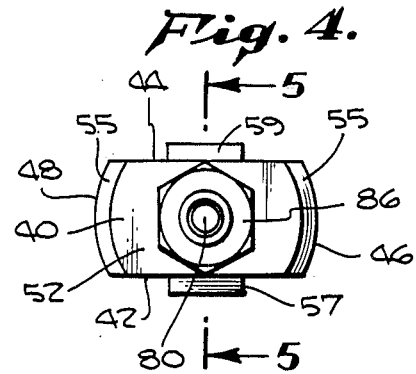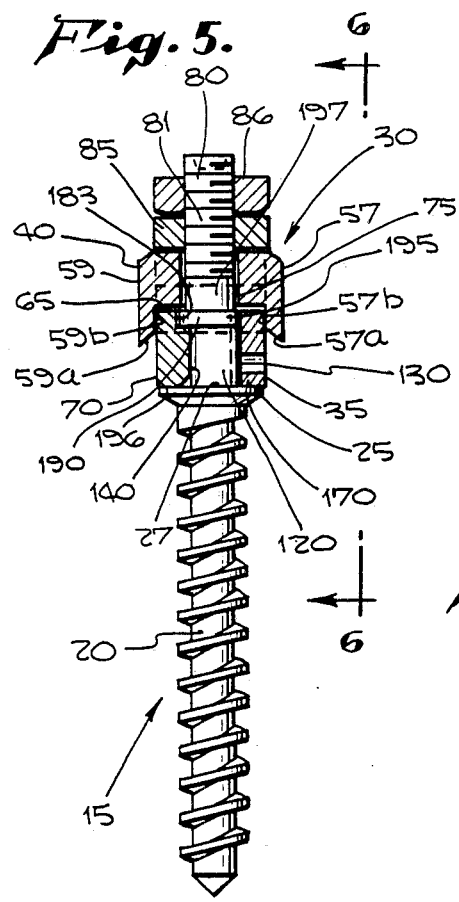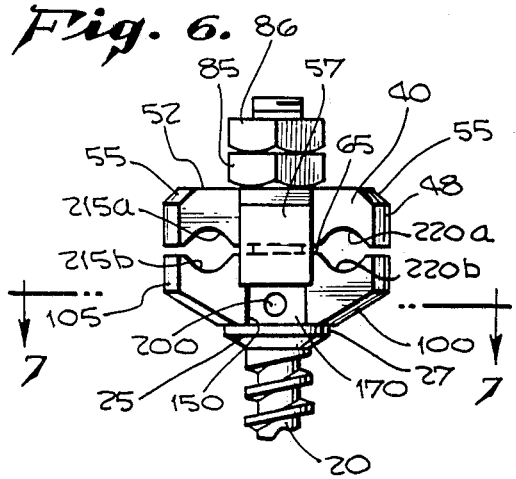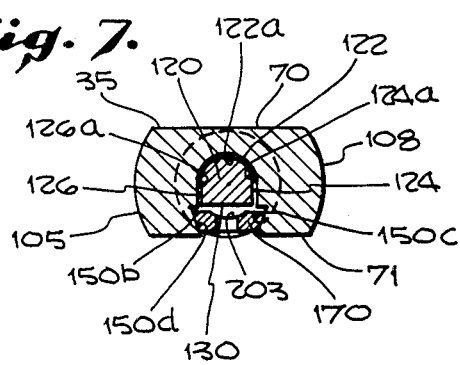

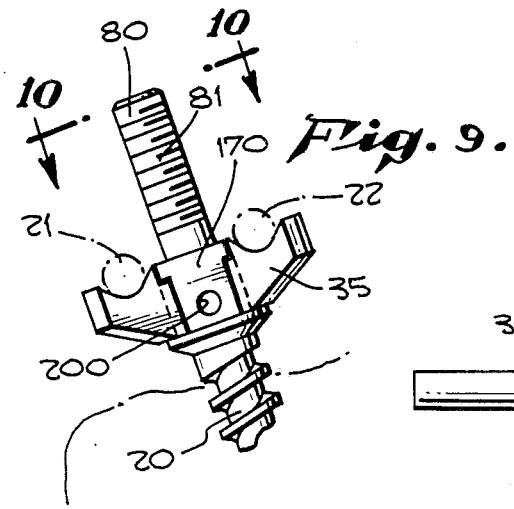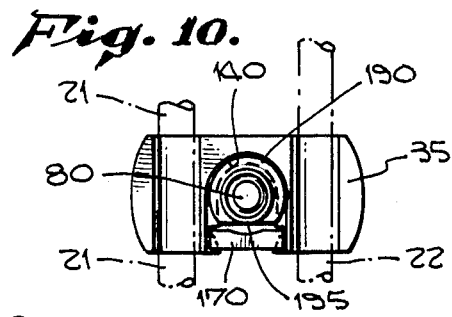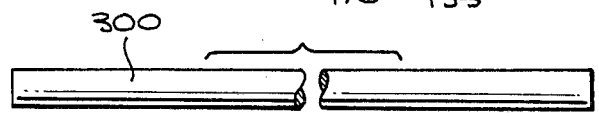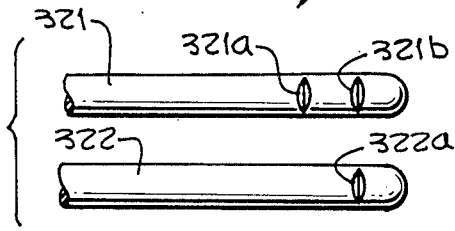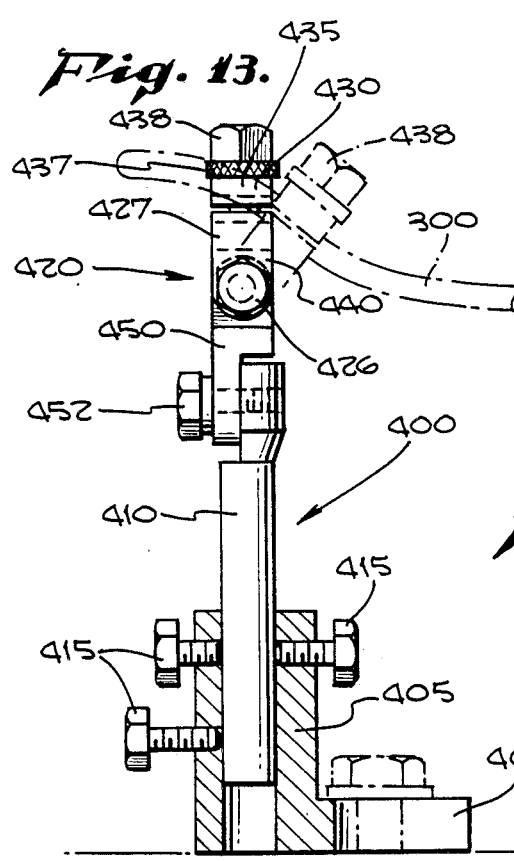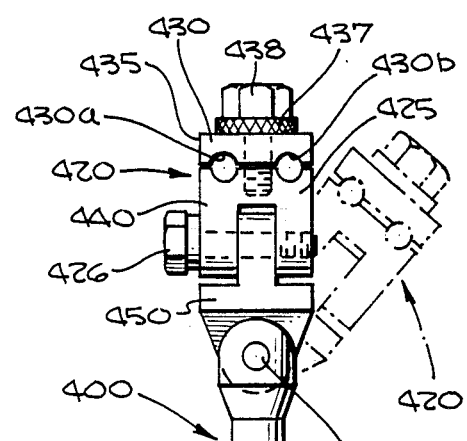

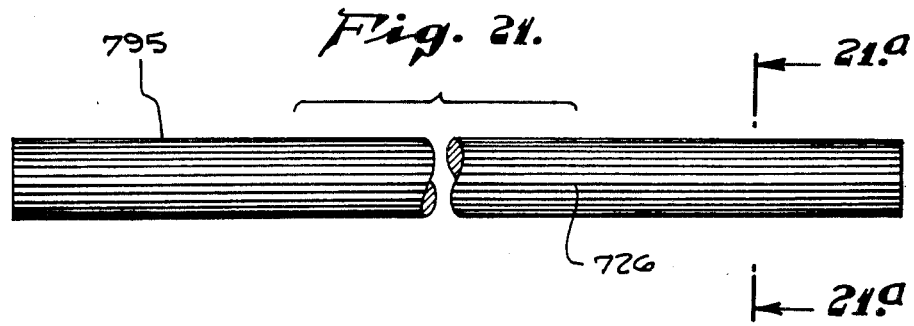
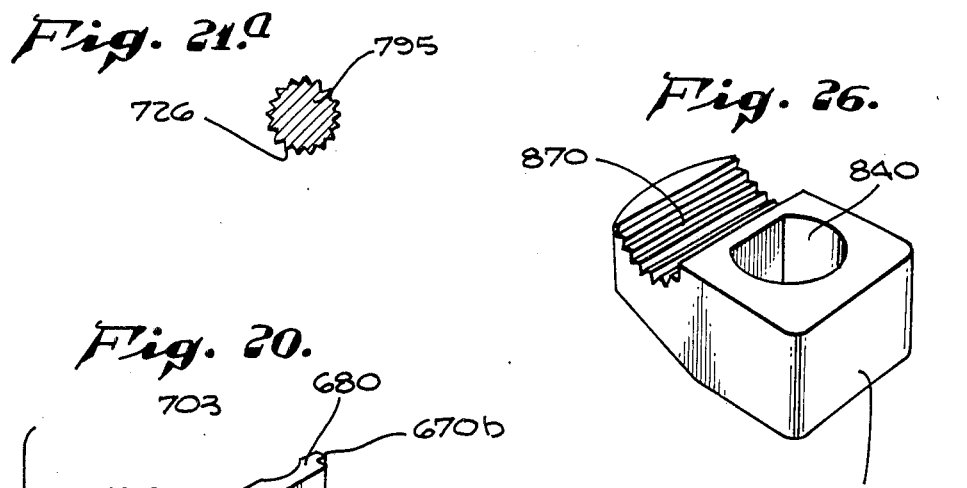
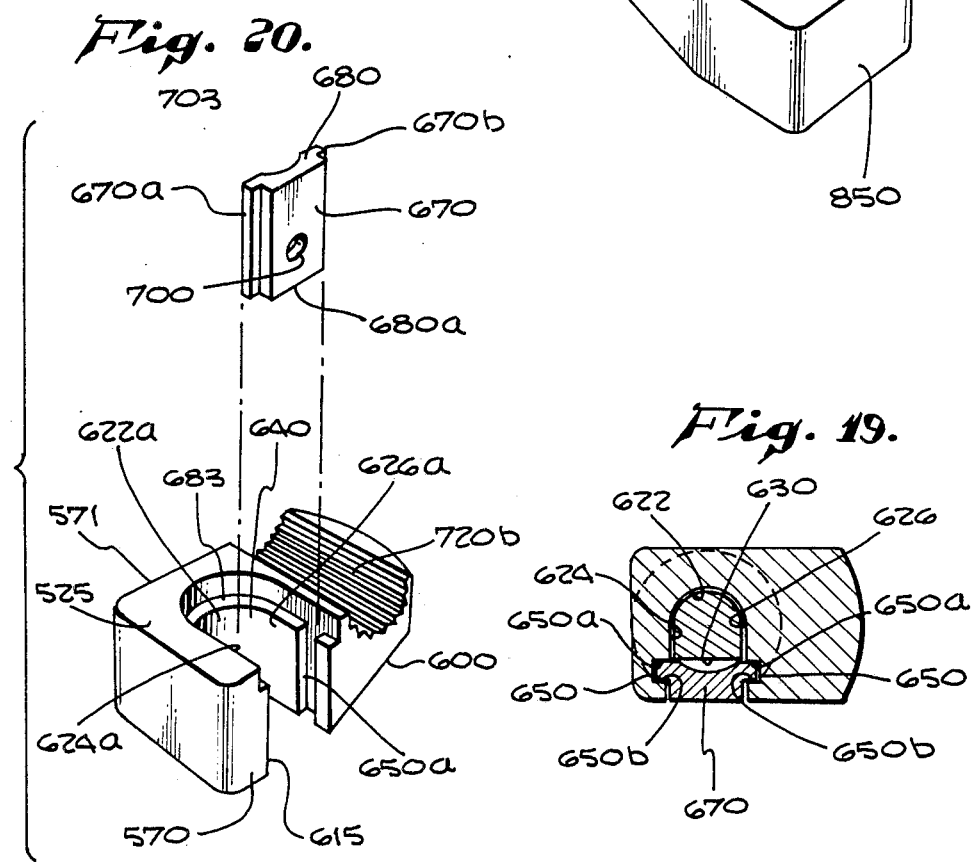

ADVANCED SPINE FIXATION SYSTEM AND METHOD

RELATED APPLICATIONS

This application is a continuation-in-part of application Ser. No. 758,294, filed on July 24, 1985.

BACKGROUND OF THE INVENTION

1. Field of the Invention

This invention relates to spinal fixation and methodology and more particularly to an improved spinal support fixation and method for the surgical treatment of spinal problems which may require correction, stabilization, adjustment of fixation of the spinal column or components thereof, and more particularly the lumbar and sacral portion of the spine, although the present invention is not limited thereto and may be used in the thoracic region of the spine.

2. Description of the Prior Art

Various types of spinal column disorders are known such as scoliosis, kyphosis, spondylolesthesis and other problems such as ruptured or slipped discs, broken or fractured spinal column, and the like. Various forms of instrumentation and procedures are known for the surgical treatment of spinal disorders, for example, Harrington Spiral Instrumentation, Bobechko Hooks, Edwards Hooks and Rod Sleeves, Luque Segmental Spinal Instrumentation and Luque Rectangles, the Dunn Anterior Spinal System, and the Kostuik-Harrington Instrumentation, to mention only a few. These and other systems are described in one or more of the following U.S. Pat. Nos.: 4,433,676; 4,369,769; 4,269,178; 4,409,968; and 4,289,123.

Some of the above systems utilize hook-type members which are merely hooked over the laminae or on selected transverse processes of the spine. Other systems, such as the Luque Segmental Spinal Rectangles, used to stabilize spinal fractures and low back fusions, use Luque wires to secure the rectangle to the spine. In some of the prior art systems, screws are used to hold a single rod in place. In other systems, screws are used to hold a slotted plate in place, the location of the screws and slots being such that the plate is moved in order to align the plate apertures or slots with the end of the screw, a nut being used to hold the plate to the screw. With this latter arrangement, sometimed referred to as a Steppee plate, there is little purchase between the plate and the screw and nut since only a small portion of the plate is engaged adjacent to the slots. Also, the plate cannot be configured to a fixed and stable curvature to follow the curvature desired by the surgeon.

As a general rule, in any of the procedures requiring the use of fixation of the type described, it is desirable to prevent rotation of the vertebral body while preventing left to right and back to front motion, in order to promote effective healing. In the case of spinal fusions for example, the fixation may be in place for six to twelve months or longer and must function properly and effectively for that period of time. If the fixation becomes loose or falls out of adjustment, it is somewhat difficult to make the necessary adjustments due to the nature of the prior art fixation. Adjustment or modification of the prior art fixation may be as major an undertaking as the original installation of the fixation due to the necessity to loosen wires or adjust hooks or rods. If, for example, a patient experiences significant pain as a result of the initial and skillful placement of the support fixation, even a minor adjustment of the prior art fixation may represent a major undertaking.

Another difficulty with the prior art fixation is that it is sometimes difficult to cause the spinal column to follow the correct or desired contour. For example, the rods used in the Harrington system or the variations thereof are normally straight rods or curved in one plane only. It is sometimes difficult to locate hooks intermediate the ends of the rod so that the vertebra between the ends of the rods are in the proper position simply because of the difficulty in properly positioning the intermediate hooks and/or forming and fixedly supporting the rods to follow the desired contour. It has been reported, for example, that Knodt rods, alar hooks or sacral bars in adult L-S fusions is associated with failure of fixation, loss of lordosis and/or nonunion in 15% to 65% of the cases. In the case of lumbo-sacral fixation, present techniques have been criticized as not providing secure fixation directly to the sacrum, not providing preservation of normal L-S angle upon distraction or compression, or not providing rigid fixation in all planes of motion.

It is also recognized that the stresses involved in the sacral and lumbar regions of the spine are greater than those in the thoracic region of the spine, i.e., T1 to T14.

BRIEF SUMMARY OF THE INVENTION

It is an object of the present invention to provide improved support fixation, principally for spinal use, and an improved methodology which achieves any one of or a combination of correction, stabilization, adjustment and fixation of the spine for the treatment of spinal problems of the type well known in the art.

It is another object of the present invention to provide improved support fixation and an improved methodology for the treatment of spinal problems associated with the lumbar-sacral region of the spine, particularly the L1-L5 and S1-S2 region thereof, as well as the thoracic region of T1-T14.

Another object of this invention is to provide a spinal support fixation and improved methodology which provides for relatively easy adjustment or partial replacement of the installed fixation without the necessity of removing or readjusting the entire in-place support fixation as compared to some of the prior art support fixation and methods.

Another object of this invention is to provide improved spinal support fixation and methodology which provides stability of internal fixation and which essentially eliminates or significantly reduces the problems of rotation of vertebra, left to right movement thereof and which provides front to back support for the portion of the spinal structure in which the support fixation is installed.

Still a further object of the present invention is the provision of an improved fixation and methodology capable of being installed in a manner which follows a desired contour while providing the proper front to back, left to right and rotational support of the selected portion of the spine. In effect, the system of the present invention is effectively custom fitted to the patient's needs in terms of curvature and which provides a rigid template to hold the spine or a portion thereof in the desired location and with the desired curvature.

Another object of the present invention is to provide a method whereby deformities of the spine may be totally or partially reduced and held in place until bone fusion occurs.

A further object of this invention is the provision of spinal fixation in which the components thereof are individually adjustable without the necessity of adjusting each or a majority of the fixation components.

The above and other objects are achieved in accordance with the present invention by a spinal support fixation system and methodology which includes the placement of unique screw clamp assemblies in selected portions of the pedicle and vertebral body of the spine, the screw clamp assemblies, in one form of the invention, supporting two spaced rods on each side of the spine and which tend to provide exceptionally good purchase in order to prevent relative movement between the rods and clamps. In general the procedure involves the usual preoperative preparation in accordance with known procedures. The appropriate section of the spinal column is exposed and the screw clamp assemblies are placed in the vertebra, as described.

In another form of the system of the present invention, wherein the rigidity of the two rod system is not needed, for example in the thoracic region of the spine (T1–T14), the screw clamp assembly is configured somewhat differently and includes serrated gripping surfaces which grip a single serrated rod. In this form, a single screw clamp assembly is associated with a single rod, as described, the serrated or equivalent mating surfaces being operative to prevent relative rotation therby providing exceptional rigidity through very firm purchase.

Preferably the screw clamp assemblies, regardless of type, are placed through the pedicle into the vertebra by positioning the screw clamp assemblies between the spinous process and the transverse process and angling the screws so as to miss the spinal cord, the corda equiva or the other sensitive nerves, blood vessels or canals. Other placements may be as determined by the attending surgeon. Positioned as described, the screw clamp assemblies are set into sufficient bone structure to be secured to the vertebra. Preferably, two screw clamp assemblies are used, one on each side of the spinous process and at the base of the adjacent transverse process of the vertebra involved. In the case of sacral placement, the screw clamp assemblies should be secured in a relatively dense bone section of the sacrum.

The screw clamp assemblies themselves are provided with a threaded end portion adapted to be screwed into the pedicle and vertebral body and include a saddle assembly which forms the rod clamping member. The saddle assembly is composed of mating half saddles which form spaced rod receiving apertures on each side of the central axis of the screw member. In one form, the apertures of the saddle halves are proportioned with respect to the dimensions of the rods which they are intended to receive such that the saddles, when firmly locked in place as will be described, firmly clamp on the rods and along a predetermined length thereof to provide firm purchase which tends to provide movement resistant purchase between the rods and the clamps. In this way the clamp members will tend to secure the rods firmly to the spinal members to which the screws are attached and tend to provide enhanced resistance against front to back, side to side and rotational movement of the supported portion of the spine.

In another form of the clamp assemblies, the saddle assembly is internally serrated and the associated single rod is externally serrated such that the saddle grips the rod firmly, with excellent purchase, in order to provide the support and resistance to movement, as described.

One of the advantages of this invention is that the spinal support system is designed to be used in a parallelogram arrangement such that there are two fairly rigid parallelograms formed on each side of the spinal column. This arrangement, as well as the designed purchase or firm gripping as a result of the use of rods which are proportioned and mounted in parallel arrangement on each side of the spinal column, tends to provide a localized rigidification which is believed to be somewhat greater than that obtained from prior art devices, especially for the L1–L5 and S1–S2 region of the spine. The fixation of this invention is intended for use primarily posteriorly in spinal support systems.

In the case of the modified form of the fixation system of the present invention, it is useable in the thoracic region, i.e., T1–T14, and again is mounted posteriorly. Since the stresses in thoracic region of the spine are not as great as in the lumbar and sacral region, a single rod may be used, as described, with the rigidity being provided by the excellent purchase achieved and enhanced through the use of serrated mating parts. Since the gripping action is along the length of the rod, as contrasted to isolated zone gripping as may be the case with Steppee plates, there is greater purchase than has been achieved heretofore. It is to be understood, however, that the two rod systems may be used in the thoracic region if the circumstances are such that a very rigid support system is needed. So too, the single rod system may be used in the sacral and lumbar region in the event that the rigidity of the two rod system is deemed unnecessary.

From a methodology standpoint, the present invention presents novel approaches in that the normal preoperative procedures are followed with a unique installation procedure which is basically the same for each form of the novel screw clamp assemblies. In the first phase, the unique screws are installed in the medically dictated positions and in the appropriate location and orientation. This usually involves location of the clamp members in the spine between adjacent spinal components, or in the sacrum, or both, as may be required for the medical problem being addressed.

After installation of the screw clamp assemblies, a temporary master is made which follows the contour which the surgeon determines is appropriate for the particular patient. This determination may require some movement of the spinal components into which the screw clamp assemblies are fixed relative to other components of the spine. The screw clamp assemblies may be initially installed in one or both sides of the spinal column and/or sacrum, in the appropriate location, as may be determined by the surgeon with respect to the particular patient involved. Thereafter, with the affected portion of the spine treated or located in the desired position, the surgeon may form a temporary master of the position in which it is desired to locate the components of the spinal column involved. The position or location of the spinal components may vary with the needs of the patient. It is preferred that all of the spinal screws be set and the desired reconstruction be completed before the start of fabrication of the temporary master rods.

The fabrication of the temporary master involves the use of a soft and easily manipulated metal rod which is formed to follow the the contour of the apertures in the lower saddle of the clamps as installed in the spine, and as determined by the surgeon. In practice, the contour of either each pair of rods or the single rod is fashioned by bending the soft and easily malleable rod or rods to follow the contour of the curve or position of the apertures of each of the clamps on one side of the spine. The same procedure is followed for the series of clamps located on the other side of the spine.

The soft rod or rods are then used to form a rod master pattern which in general involves the positioning of a rod master clamp assembly in the proper orientation to receive the soft rod. The rod master clamp, of which there are several located on a bench bending fixture and which match in number the number of screw clamp assemblies, are fabricated to be movable axially, rotationally and pivotable in two directions. Each rod master clamp includes a saddle assembly similar to the screw clamp, such that the apertures of the rod master clamps are arranged to duplicate the contour of the screw clamps, using the soft rods as the master. Once the rod master clamps are oriented to match the contour of the screw clamps, a rigid rod is then formed to follow the contour of the rod master clamps. This sequence of operations involves bending the rigid rod such that its configuration matches and fits the contour of the rod master clamps. Proper contour matching is checked against the rod master clamps with are a replication of the position and attitude of the screw clamps. Once the proper matching contour is achieved, the procedure is repeated with the second rod of the set to be affixed to the one set of screw clamps, if a dual rod system is used. Once the pair or the single rod is fashioned to the contour of the master clamps, the pair of rods or the single rod may be installed in the proper position in the screw clamps and checked for proper fit. Excess rod length may be cut off at this point, if that is necessary, and the rod or rods are seated in the rod receiving apertures of the proper clamp and the saddles are locked in place on the mating rod or rods. This procedure is then repeated for the other rod or the second set of rods, including the use of soft and pliable rods or rods each configured to follow the contour of the second set of screw clamps. A second rod or set of rigid rods is fashioned of the proper contour, cut to length if necessary, and installed in the second set of screw clamps and locked in place. The same rod master clamps may be used for the dual and single rod system, as will be apparent.

The result of the procedure, in the case of a dual rod system, is the formation of two spaced parallelograms on each side of the spinal column in which rigid and properly contoured rods are securely gripped and purchased by the saddles along a portion extending generally axially along the spine. These spaced parallelograms offer significant strength and support against front to back, side to side and rotational movements of the portion of the spinal column involved. In large measure, the strength of the support system is due to the excellent purchase achieved between the rods and the apertures in the saddles and the parallelogram geometry which itself provides a rigidifying structure.

In the case of a single rod system, there is again a significant rigidity provided since the saddles are serrated and firmly purchase on the serrated rods to prevent relative rotary motion between the clamp assemblies and the associated rod. Since there is fixation and support on each side posteriorly of the selected portion of the spine, the axially rigid and rotationally rigid system is effective to provide the support and fixation required. It is to be understood that the surgeon may wish to use both a double and a single rod system, depending upon the particular case, i.e., high localized rigidity.

After installation, the procedure is completed with the post-operative protocol being that set by the attending surgeon. In the event of a need to make any adjustment of the installed support system, be it a single or dual rod system, one or more of the saddle assemblies may be removed without the necessity of undoing the entire support system and adjusting the screw clamp as may be needed, followed by relatively easy remounting of the saddles to purchase again on the rods, as will be described in detail.

It is apparent from the foregoing brief description that the present invention offers many advantages over the prior art spinal support fixation systems and methodology. These and other advantages and other objects are made more clearly apparent from a consideration of the several forms in which the invention may be embodied. Such forms are illustrated in the drawings accompanying and forming part of the present specification. The forms described in detail are for the purpose of illustrating the general principles of the present invention; but it is to be understood that such detailed description is not to be taken in a limiting sense.

BRIEF DESCRIPTION OF THE DRAWINGS

FIG. 4 is a view, partly in section and partly in elevation, taken along the line 4—4 of FIG. 3 and illustrating the details of the screw clamp in accordance with this invention;

FIG. 5 is a view, partly in section and partly in elevation, taken along the line 5—5 of FIG. 4;

FIG. 6 is a view, partly in section and partly in elevation, taken along the line 6—6 of FIG. 5;

FIG. 7 is a view, in section, taken along the line 7—7 of FIG. 6;

FIG. 8 is a developed view of the lower saddle assembly of the screw clamp in accordance with the present invention;

FIG. 9 is a view partly in section and partly in elevation indicating the manner of location of the rods in the apertures of the saddle assembly in accordance with this invention;

FIG. 10 is a plan view as seen along the line 10—10 of FIG. 9;

FIG. 11 is a diagrammatic view of the soft rods used to form the master clamp contour in accordance with this invention;

FIG. 12 is a diagrammatic view of the rigid rods used in the spinal support fixation in accordance with the present invention;

FIG. 13 is a side view in perspective of the master clamp assembly used to form the proper contour of the support rods in accordance with the present invention;

FIG. 14 is another view in perspective of the master clamp assembly illustrated in FIG. 13;

FIG. 19 is a sectional view taken along the line 19—19 of FIG. 18;

FIG. 20 is a developed view of the lower saddle assembly of the modified form of screw clamp assembly previously illustrated;

FIG. 21 is a view in perspective of a serrated rod for use with the modified screw clamp assembly of the present invention;

FIG. 21a is a sectional view taken along the line 21a-21a of FIG. 21;

DETAILED DESCRIPTION OF THE PREFERRED EMBODIMENTS

Figure 1:
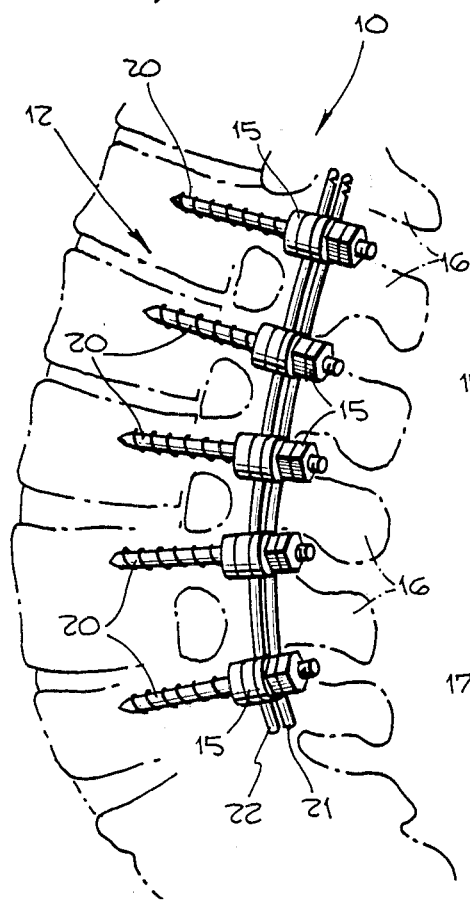
FIG. 1 is a diagrammatic view, as seen laterally, of the spinal support fixation system of the present invention installed in a portion of the spinal column.
Figure 2:
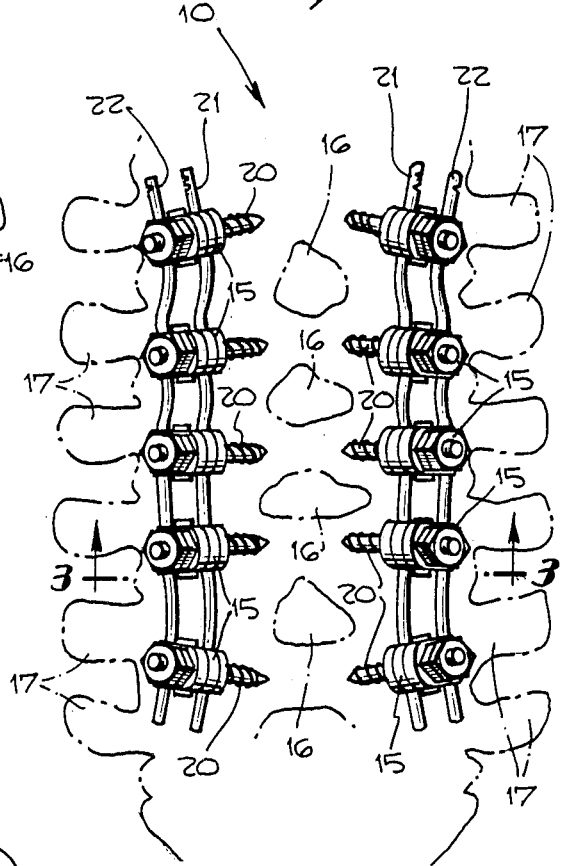
FIG. 2 is a diagrammatic view, as seen posteriorly, of the spinal support fixation system illustrated in FIG. 1.
Figure 3:
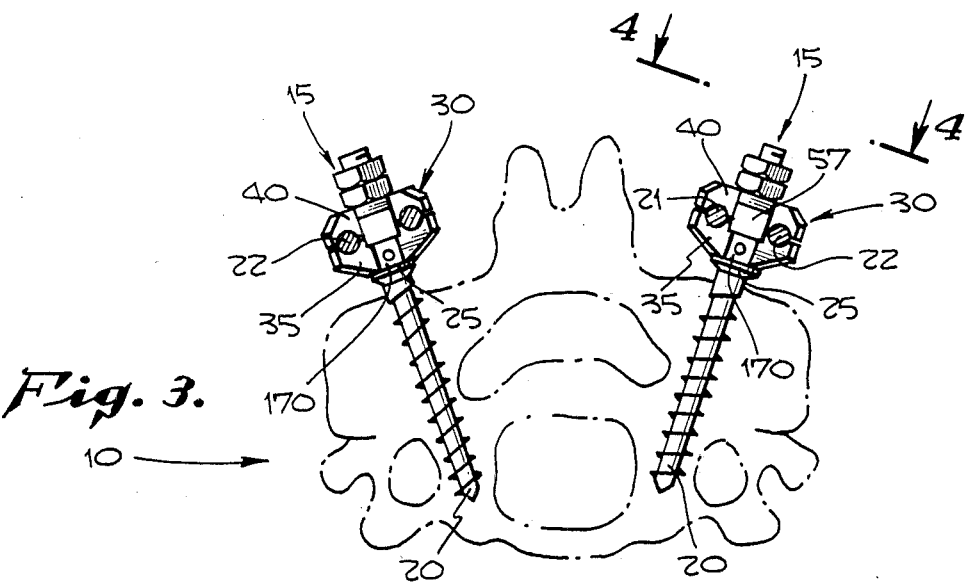
FIG. 3 is a view, partly in section and partly in elevation, taken along the line 3—3 of FIG. 2.

Referring to the drawings which are not to scale and which illustrate preferred forms of the present invention, FIGS. 1 and 2 illustrate somewhat diagrammatically the spinal support system 10 of the present invention installed in the spinal column generally designated 12. As illustrated, the spinal support system 10 includes a plurality of screw clamp assemblies 15 each of which is preferably located between the spinous process 16 and the associated transverse process 17 on each side of the spinous process and in the posterior portion of the spinal column. This relative position of the screw clamp assemblies is preferred since the threaded end 20 of the screw clamp is located through the pedicle, a bony portion of the vertebra which will hold the clamps in place. As seen, there are two screw clamp assemblies placed in each vertebra and each of the screw clamp assemblies supports and firmly holds spaced rods 21 and 22. The support system of this invention is especially adapted to be used in the L1-L5 and S1-S2 region of the spine, although its use is not limited thereto. FIG. 1 also illustrates the contour and curvature which may be achieved with the present invention.

Positioned as described, the spinal support system 10 provides a markedly rigid support system which tends to inhibit left to right, front to back and rotational movements of the supported portion of the spinal column. The rigidity of the system is due in part to the fact that the rods 21 and 22 cooperate with the clamps 15 to form a parallelogram on each side of the spinal column, a rigidity which is enhanced since there is purchase on each of the rods at spaced portions along the length of the rods, a gripping type of action which has significant advantages and which will be explained in detail later.

Referring now to FIGS. 3-8, the screw clamp assemblies include a threaded end 20 for placement into the bony structure of the vertebra of the spine, as may be determined by the surgeon. The preferred location is through the pedicle, although other regions may be used, especially in the sacral region. The screw clamp assemblies may be inserted directly or placed in a pre-drilled opening dimensioned to receive the threads so as to secure the screw firmly into an appropriate support structure of the spine. The configuration of the screw threads is well known and is that normally used for screw members intended to be implanted in bone structures. The leading screw end of the clamp terminates in a tapered flange 25, which faces the screw threads 20, as best seen in FIG. 6, the flange including a flat surface pocket portion 27 opposite the threaded end 20 for reception of a saddle assembly generally designated 30. The provision of a tapered flange permits the saddle assembly to be positioned close to the vertebra into which the screw is positioned.

The saddle assembly 30, in accordance with a preferred form of the invention, is removable from the screw and is preferably formed of a lower half 35 and an upper half 40 as seen in FIGS. 4, 5 and 6. Overall the outer surface of the saddle assembly includes flat front and rear surfaces 42 and 44 and curved or rounded end faces 46 and 48, as seen in FIG. 4, a geometry which facilitates positioning of the screw clamp assemblies in tight regions of the spinal structure. As also seen in FIG. 4 the upper or top surface 52 of the upper half 40 of the saddle assembly 30 is beveled at 55 to eliminate sharp peripheral side edges.

Preferably integrally formed on the upper half 40 of the saddle assembly are two depending fingers 57 and 59, see FIGS. 4 and 5, one located on each face 42 and 44, and dimensioned axially to extend somewhat below the upper surface 65 of the lower half 35 of the saddle assembly. The lower end of each of the fingers terminates in a reverse taper 57a and 59a which assists in camming the upper half over the lower half during the assembly of the two halves, as will be described. The length of the fingers is preferably such that the inner surfaces 57b and 59b of each of the fingers is opposite upper portion of the faces 70 and 71 of the lower half 35 of the saddle assembly, as seen in FIGS. 5 and 6. The upper half 40 of the saddle assembly includes an opening 75, as seen in FIG. 5, so that the other end 80 of the screw clamp may pass therethrough. The end 80 of the screw clamp includes a second threaded end 81, spaced from the flange 25 and whose thread configuration may be that of a machined screw. Received on the threaded end 81 is a saddle locking assembly in the form of a securing nut 85 and a locking nut 86, as seen in FIGS. 5 and 6, and used to secure the two halves of the saddle assembly together.

Referring now to FIGS. 5 to 8, the lower half saddle 35 includes a lower surface 100 which is tapered upwardly, as shown, and which follows the contour of the face of the flange 25. The faces 70 and 71 of the lower saddle half are dimensioned such that the upper and lower halves have the same face to face dimensions. The lower half, like the upper half, includes rounded side faces 105 and 108 which follow the shape of side faces 46 and 48 of the upper half. Thus, when assembled together, the upper and lower halves of the saddle assembly include a flat upper surface, a beveled and curved edge, a curved side face and a tapered lower face, as illustrated in FIG. 4. Overall, this provides an outer surface geometry which facilitates location of the screw clamp in regions of the spine in which the anatomy of the patient is such there is a minimal amount of room for the surgeon to work.

While the upper half of the saddle assembly is intended to be installed by placing the upper half over the threaded end 80 of the screw clamp, the lower half is designed to be assembled by insertion laterally of the shaft of the screw clamp, followed by assembly of the upper half and appropriate locking of the saddle assembly. Thus, as seen in FIGS. 5, 7 and 8, the lower half saddle 35 is provided with a side opening 115 for sideways insertion on the shaft 120 of the screw clamp 15. As shown in FIG. 7, this portion of the shaft, forming the lower half saddle receiving portion of the shaft, is formed with a partial circular or semi-circular shape 122, parallel spaced side faces 124 and 126 and a flat front face 130. The lower half saddle includes a complimentary shaped interior opening 140 having a partial circular shape 122a, parallel side faces 124a and 126a and an open front portion, as illustrated in FIG. 8.

The side opening 115 is formed with a vertically extending slot 150, which includes vertically extending walls 150a and 150b, each including an adjacent reverse tapered vertically extending wall segment 150c and 150d. Receivable within the vertical slot 150 is a generally T-shaped lower half saddle lock member 170, the latter including tapered side faces 170a and 170b which form a dove-tail lock with the opposed wall segments 150c and 150d, as seen in the sectional view of FIG. 7. The cross-member 180 of the T-shaped lower saddle lock member 170 is received in a counterbore 183 formed in the upper surface 52 of the lower half 35 of the saddle assembly. To locate the lower half 35 of the saddle properly on the shaft portion 120 of the screw clamp, the shaft portion 120 includes a shoulder 190, as shown in FIG. 5. It is understood that the lock member and the configuration of the receiving lower half saddle may be of the configuration hereinafter described.

The shoulder 190 is generally circular and includes a flat face 195, see FIG. 10, which forms a continuation of the face 130. The dimension from the upper surface of the flange 25 to the underside of the shoulder 190 is approximately that of the axial dimension from the lower center surface of the lower half saddle 35 to the upper inside surface of the counterbore 183. The lower center surface 196 of the lower half of the saddle is flat in order to seat on the flat upper surface of the of the flange, as seen in FIG. 6, for example. Immediately above the shoulder 190 is a small non-threaded section 197 of the shaft, the section 197 being located between the threaded end 81 and the top of the shoulder 190.

Proper assembly of the lower half saddle 35 to the screw involves alignment of the opening 115 axially with respect to the shoulder 190 and sliding the lower saddle in place on the shaft such that the counterbore is positioned to receive the shoulder. The curved surface 122a of the lower saddle should be facing the curved section 122 of the shaft such that the curved and parallel side faces are in engagement. Thus located, the saddle lock member 170 is inserted in the keyway slot 150. To assist in inserting and removing the lower saddle lock 170, the latter is provided with an aperture 200, as seen in FIGS. 6 and 9, and to which an appropriate tool may affixed for manipulation of the lock member. Further, the face 203 of the saddle lock 170 which faces the the shaft 120 is axially grooved, as indicated in FIG. 7, to fit over the threaded portion 81 of the screw clamp. Properly positioned, the shoulder 190 and the flange 25 operate to prevent axial movement of the lower half saddle while the lower saddle lock prevents lateral movement off the shaft.

The upper saddle half may then be assembled over the shaft end 80 such that the finger facing the lower saddle lock overhangs the T-section 180 of the lower saddle lock to prevent movement of the saddle lock vertically out of the keyway. To facilitate assembly of the upper saddle half, the latter is constructed in a symmetrical fashion such that either face may be positioned over the saddle lock, as seen in FIGS. 4 and 5.

One of the advantages of the present invention is that the saddle lock assembly is designed to effect a firm gripping purchase on the rods 21 and 22 along a portion of the length thereof. To this end, each of the upper and lower halves of the saddle assembly are provided with mating grooves 215a and 215b and 220a and 220b, the pairs of grooves being located on each side of the shaft. The grooves are dimensioned to be slightly smaller in dimension than the circumferential dimension of the rods. For example, the diameter of the apertures in the saddle assembly may be 0.154 of an inch while the rod diameter may be 0.155 of an inch. In general, the rod diameter and the diameter of the apertures are coordinated to provide an interference fit of 0.0010 of an inch between the rod and the associated groove when the screw clamp assembly is tightened on the rods. In part, it is this interference fit which provides good purchase between the clamp assembly and the associated rods and thus provides excellent internal fixation. It is also to be noted that the grooves are located to clear the shaft thereby permitting the shaft to be removed through the spaced rods. The rods and the faces of the grooves may be serrated, as will be described in order to provide increased enhanced purchase.

Referring to FIGS. 9 to 12, enhanced purchase is achieved by the fact that the portions of the screw clamps which grip the rods, effectively grip the latter by an interference fit along that portion of their length representing the face-to-face dimension of the saddle halves. This type of purchase along the length of the rods is in sharp contrast to line contact as may exist with some of the prior art devices. The face-to-face dimension may be 0.375 of an inch, for example, with the center line of the grooves being spaced 0.460 of an inch, i.e., 0.230 of an inch on each side of the center line. In this way, the upper saddle half may be removed, the lower saddle lock 170 may be removed by lifting it vertically through the spaced rods 21 and 22 and the lower saddle half is slipped laterally out from under the rods, as indicated by the arrow in FIG. 10. Reassembly of the in-place screw clamp is just the reverse.

The screw clamp 15 may be installed in a component of the spinal structure with or without the saddle assembly attached. If the saddle assemby is not attached a tool may be used to grip the flat faces 122, 126 and 130 of the shaft to form a driving connection to the screw member. Alternatively, a tool may be used on the threaded end 81, with or without the saddle assembly present. Once the screw members are positioned in the appropriate location in the spinal structure and to the proper depth, the shafts are rotated so that the apertures of the saddle assembly are in alignment, even though they need not necessarily be in the same plane. There may be some tilt to the plane to which the grooves are located.

Thereafter, a soft rod, as for example, soft aluminum alloy, preferably of the same dimensions of the final installed rods, is assembled to the installed and the in-place screw clamp assemblies by starting at the center clamp of the set and working in each direction axially along the spine. The soft rods are preferably cylindrical solid rods as indicated at 300 of FIG. 11. The length of the soft rods 300 may vary depending upon the need. Since these rods are soft and easily manually formed, they are located in the grooves of the lower saddle assembly and locked in place with the upper half saddle and lock to form a replication or master of the relative position of the apertures of the saddle assemblies. It is preferred that the two rods for each set of screw clamp assemblies be formed at the same time so that a true relative replication may be made.

Ultimately, relatively rigid rods such as 321 and 322 illustrated in FIG. 12, and to be described in detail, will be installed in the screw clamp assemblies. For ease of identification, the rods are marked, as by notches 321a, 321b and 322a.

In effect the rods 300 form a temporary master to be used to configure the rods 321 and 322 to replicate the position of the screw clamp saddle assembly apertures. To form the rod master pattern, a plurality of rod master clamp assemblies 400, as shown in FIGS. 13 and 14 are used. The rod master assemblies are mounted on a suitable support, not shown, such that there are a sufficient number of such units to match the number of installed screw clamps and in the same general alignment.

Each master clamp assembly includes a foot 402 apertured to receive a bolt to lock the master clamp to a support, as illustrated. The foot includes a vertical support 405 which receives a head mounting shaft 410. The shaft 410 may be positioned axially and rotationally in the support to achieve the desired orientation and height and locked into place by the bolts 415. This is done with each of the master clamps.

Carried by the shaft 410 is a double articulating head assembly 420 which includes a master clamp head 425 pivotable in two directions, as indicated in the dotted lines of FIG. 13, and which may be locked in place by bolt 426. The master clamp head includes a master clamp 430 which essentially replicates the saddle assembly of the screw clamp insofar as the position of the apertures 430a and 430b are concerned. The master clamp includes an upper removable saddle 435 which may be secured in place by the lock system composed of a knurled fitting 437 and lock nut 438. A lower saddled 440 is also provided and is likewise dimensioned to match the dimensions of the lower saddle half of the screw clamp assembly. The master head clamp is mounted on an intermediate articulating head 450, pivotable in two directions, as indicated in dotted lines in FIG. 14, and which may be locked in place by the nut 452. The intermediate head 450 and the master head clamp 425 are each independently movable and adjustable.

In substance, the soft metal rods which form the temporary masters are used to position the master head clamps 425 of each of the assemblies such that apertures 430a and 430b follow the contour of the soft metal masters and thus the contour of the screw clamp saddle assembly. In practice, each assembly is relatively easily adjusted, as above described, to replicate the soft master contour and thus the that of the screw clamps. After the replication process is finished, the soft master rods are removed, without changing the settings, and the rods 321 and 322 are shaped to follow the contour of the master clamps. This may be accomplished with a bending tool, again starting at the center master clamp of the series and progressing towards the ends. After the rigid rods are shaped, they are assembled to the screw clamp assemblies, which are then locked in place, as described, with the result being the rigid support system already described. To assure that the lock nut does not back off, the end threads may be slightly deformed.

Although not specifically mentioned, it is understood that the procedure is carried out in the aseptic conditions of the operating suite and all instrumentation and components are in a sterile condition.

If any adjustment is needed, due to the structure of the screw clamps, it is relatively easy to disassemble one of the clamps from the rods by backing off the lock nut and the securing nut, removing the upper saddle half, removing the lower saddle lock and sliding the lower saddle off the shaft. The screw clamp shaft may be reset as needed or any other adjustments may be made as needed, without having to undo any other clamp or attachment to the rods. In some of the prior art systems, it may have been necessary to undo the entire support system, especially in the case of hook or wire type assemblies, in order to effect an adjustment.

Figure 15:
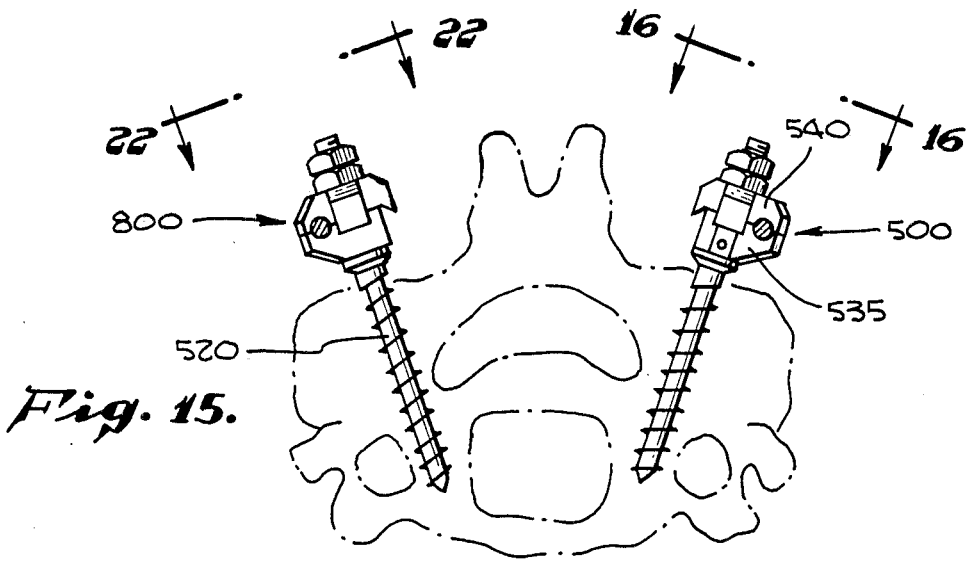
FIG. 15 is a diagrammatic view of another form of screw clamp assembly in accordance with this invention, two forms being illustrated.

The form of screw clamp assembly illustrated in FIG. 15 is for a single rod system and two different forms are illustrated, 500 with a lower saddle lock and 800 to be described. As illustrated, the single rod screw assemblies may be positioned such that the rod is outboard, as shown, or arranged inboard, or one inboard and one outboard.

Figure 18:
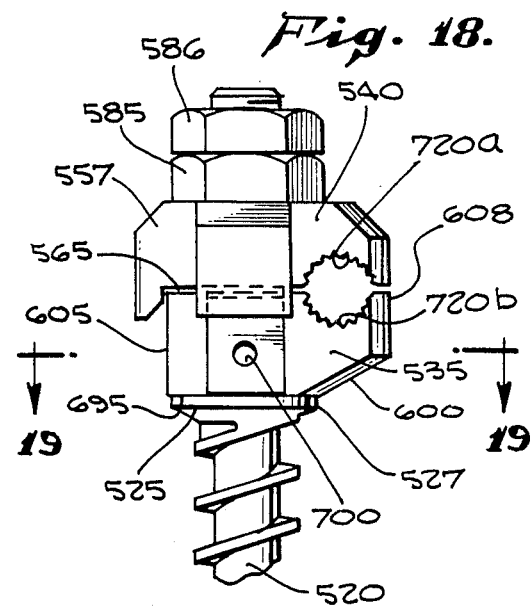
FIG. 18 is a view, in elevation, as seen along the line 18—18 of FIG. 17.
Figure 25:
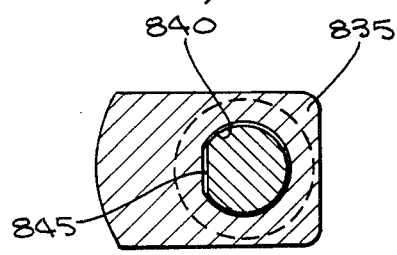
FIG. 25 is a sectional view taken along the line 25—25 of FIG. 24.
Figure 22:
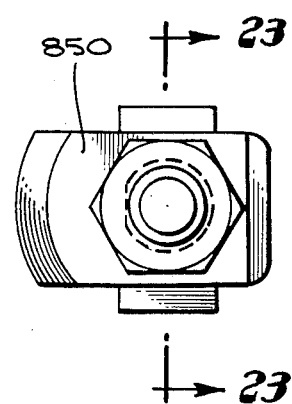
FIG. 22 is a view, partly in section and partly in elevation, taken along the line 22—22 of FIG. 15 and illustrating the details of one modified form of screw clamp in accordance with this invention.
Figure 23:
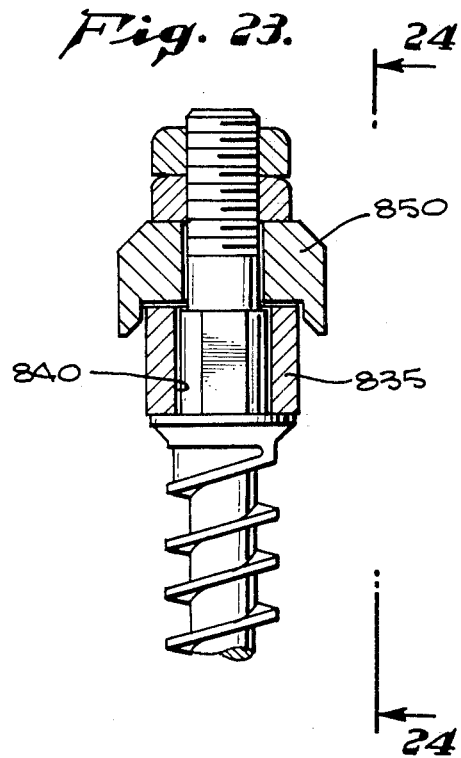
FIG. 23 is a view, parly in section and partly in elevation, as taken alon the line 23—23 of FIG. 22.
Figure 24:
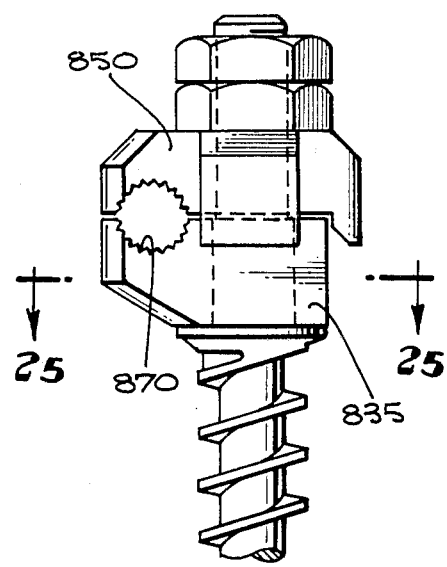
FIG. 24 is a view in elevation as seen along the line 24—24 of FIG. 23.

The screw clamp assembly 500 is somewhat similar to that previously described and includes a threaded end 520 for placement, the configuration of the threads being well known and as already described. The leading screw end of the clamp terminates in a tapered flange 525, which faces the screw threads 520, as best seen in FIG. 18, the flange including a flat surface pocket position 527 opposite the threaded end 520 for reception of a saddle assembly generally designated 530. The provision of a tapered flange permits the saddle assembly to be positioned close to the vertebra into which the screw is positioned.

Figure 16:
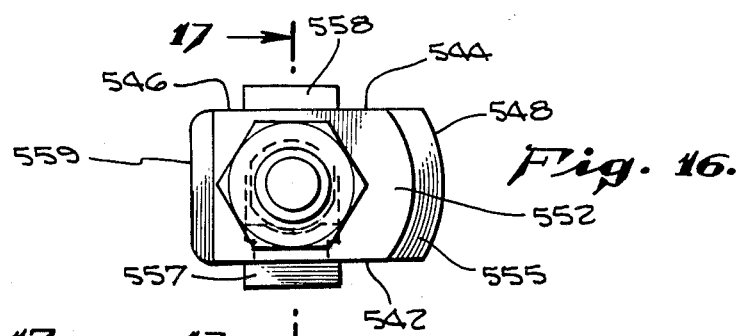
FIG. 16 is a view, partly in section and partly in elevation, taken along the line 16—16 of FIG. 15 and illustrating the details of one modified form of screw clamp in accordance with this invention.
Figure 17:
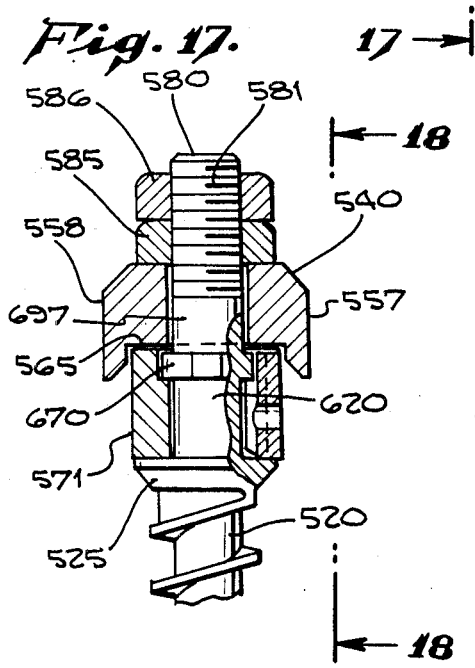
FIG. 17 is a view, partly in section and partly in elevation, taken along the line 17—17 of FIG. 16.

The saddle assembly 530, in accordance with a preferred form of the invention, is removable from the screw and is preferably formed of a lower half 535 and an upper half 540 as seen in FIGS. 15, 17 and 18. Overall the outer surface of the saddle assembly includes flat front and rear surfaces 542 and 544 and a generally flat end face 546 and a rounded end face 548, as seen in FIG. 16, a geometry which facilitates positioning of the screw clamp assemblies in tight regions of the spinal structure. As also seen in FIG. 16 the upper or top surface 552 of the upper half 540 of the saddle assembly 530 is beveled at 555 to eliminate sharp peripheral side edges.

Preferably integrally formed on the upper half 540 of the saddle assembly are front and back depending fingers 557 and 558 and a side depending finger 559, see FIGS. 15, 16 and 18, each dimensioned axially to extend somewhat below the upper surface 565 of the lower half 535 of the saddle assembly. The lower end of each of the fingers terminates in a reverse taper, as illustrated, which assists in camming the upper half over the lower half during the assembly of the two halves, as already described.

The upper half 540 of the saddle assembly includes an opening 575, as seen in FIG. 17, so that the other end 580 of the screw clamp may pass therethrough. The end 580 of the screw clamp includes a second threaded end 581, spaced from the flange 525 and whose thread configuration may be that of a machined screw. Received on the threaded end 581 is a saddle locking assembly in the form of a securing nut 585 and a locking nut 586, as seen in FIGS. 17 and 18, and used to secure the two halves of the saddle assembly together.

Referring now to FIGS. 17 to 20, the lower half saddle 535 includes a lower surface 600 which is tapered upwardly, as shown, and which follows the contour of the face of the flange 525. The faces 570 and 571 of the lower saddle half are dimensioned such that the upper and lower halves have the same face to face dimensions. The lower half, like the upper half, includes a flat side face 605 and a rounded side face 608 which follow the shape of the corresponding side faces of the upper half for the reasons already noted. Overall, this provides an outer surface geometry which facilitates location of the screw clamp in regions of the spine in which the anatomy of the patient is such there is a minimal amount of room for the surgeon to work.

While the upper half of the saddle assembly is intended to be installed by placing the upper half over the threaded end 580 of the screw clamp, the lower half is designed to be assembled by insertion laterally of the shaft of the screw clamp, followed by assembly of the upper half and appropriate locking of the saddle assembly. Thus, as seen in FIGS. 17, 19 and especially 20 the lower half saddle 535 is provided with a side opening 615 for sideways insertion on the shaft 620 of the screw clamp. As shown in FIG. 19, this portion of the shaft, forming the lower half saddle receiving portion of the shaft, is formed with a partial circular or semi-circular shape 622, parallel spaced side faces 624 and 626 and a flat front face 630. The lower half saddle includes a complimentary shaped interior opening 640 having a partial circular shape 622a, parallel side faces 624a and 626a and an open front portion, as illustrated in FIG. 20.

The side opening 615 is formed with spaced vertically extending slots 650, each of which includes vertically extending generally parallel walls 650a and 650b. Receivable within the vertical slot 650 is a lower half saddle lock member 670, somewhat different in configuration from the lock member 170 previously described. The saddle lock member 670 includes laterally extending shoulders 670a and 670b received in the slot 650 as seen in the sectional view of FIG. 19. The dimension from the top face 680 to the bottom face 680a of the lower saddle lock member 670 is such that when positioned in place, the top face is even with a counterbore 683 formed in the upper surface 552 of the lower half 535 of the saddle assembly. The lower face 680a rests on the uuper face of flange 527. To locate the lower half 535 of the saddle properly on the shaft portion 620 of the screw clamp, the shaft portion 620 includes a shoulder 690, as shown in FIG. 17.

The shoulder 690 is generally circular and the dimension from the upper surface of the flange 525 to the underside of the shoulder 690 is approximately that of the axial dimension from the lower center surface of the lower half saddle 535 to the upper inside surface of the counterbore 583. The lower center surface 696 of the lower half of the saddle is flat in order to seat on the flat upper surface of the of the flange, as seen in FIG. 18, for example. Immediately above the shoulder 690 is a small non-threaded section 697 of the shaft, the section 697 being located between the threaded end 581 and the top of the shoulder 690, as seen in FIG. 17.

Proper assembly of the lower half saddle 535 to the screw involves alignment of the opening 615 axially with respect to the shoulder 690 and sliding the lower saddle in place on the shaft such that the counterbore is positioned to receive the shoulder. The curved surface 622a of the lower saddle should be facing the curved section 622 of the shaft such that the curved and parallel side faces are in engagement. Thus located, the saddle lock member 670 is inserted in the keyway slot 650. To assist in inserting and removing the lower saddle lock 670, the latter is provided with an aperture 700, as seen in FIGS. 18 and 20, and to which an appropriate tool may affixed for manipulation of the lock member. Further, the inner face 703 of the saddle lock 670 which faces the the shaft 620 is axially grooved, as indicated in FIG. 19, to fit over the threaded portion 581 of the screw clamp. Properly positioned, the shoulder 690 and the flange 525 operate to prevent axial movement of the lower half saddle while the lower saddle lock prevents lateral movement off the shaft.

The upper saddle half may then be assembled over the shaft end 580 such that the finger facing the lower saddle lock overhangs the lower saddle lock to prevent movement of the saddle lock vertically out of the keyway.

One of the advantages of the present invention is that the saddle lock assembly is designed to effect a firm gripping purchase on the rod, to be described, along a portion of the length thereof. To this end, each of the upper and lower halves of the saddle assembly are provided with mating grooves 720a and 720b, the grooves being located on one side of the shaft. In this form, the grooves are formed with serrations along their length, as illustrated and seen better in FIG. 20. The number of serrations may be as desired, and 50 serrations around the inner mating surfaces may, for example, be used. When assembled to the mating rod, to be described, there is excellent purchase and effectively no relative rotation between the mating parts.

This type of purchase along the length of the rod is in sharp contrast to line contact as may exist with some of the prior art devices. The face-to-face dimension may be 0.375 of an inch, for example, with the center line of the grooves being spaced 0.460 of an inch, i.e., 0.230 of an inch on each side of the center line. In this way, the upper saddle half may be removed, the lower saddle lock 670 may be removed by lifting it vertically and the lower saddle half is slipped laterally out from under the rod, as already described. Reassembly of the in-place screw clamp is just the reverse.

The screw clamp may be installed in a component of the spinal structure with or without the saddle assembly attached. If the saddle assembly is not attached a tool may be used to grip the flat faces 622, 626 and 630 of the shaft to form a driving connection to the screw member. Alternatively, a tool may be used on the threaded end 581, with or without the saddle assembly present. Once the screw members are positioned in the appropriate location in the spinal structure and to the proper depth, the shafts are rotated so that the apertures of the saddle assembly are in alignment, even though they need not necessarily be in the same plane. There may be some tilt to the plane in which the grooves are located.

FIGS. 21 and 21a illustrate the serrated rod 795 which may be used with a single rod system. As illustrated, the serrations 796 extend around the entire periphery and all the way lenthwise and correspond in number to those of the screw clamp. To increase the purchase, the rod may be dimensioned such that there is a tight interference fit between the mating parts.

The form of screw clamp assembly illustrated at 800 is similar to screw clamp assembly 500 but differs in the structure of the lower saddle; in all other respects the two are the same, except as noted. Referring to FIGS. 22 to 25, the lower saddle 835 is essentially the same as 535 except that there is no saddle lock assembly and the lower saddle 835 is assembled over the screw rather than being inserted sideways. Thus the lower saddle includes an aperture 840 which includes a flat 845 which mates with a flat formed on the described receiving portion of the screw member for the purpose of orientation. The upper saddle 850 may be as described in connection with 540 and is in fact essentially identical and interchangeable with either lower saddles of the two single rod systems described. Again, the mating surfaces of the upper and lower saddles are serrated as indicated at 870 for the reasons described. The assembly, removal and adjustment of this form of screw assembly is apparent from the prior detailed description.

Like the forms already described, the single rod systems described are placed in the patient, as described, and the mastering technique already described is followed. In effect, the procedure and advantages of the dual rod system are applicable to the single rod system, as is apparent from the prior detailed discussion.

Since the type of support may vary depending upon the patient, the clamps and rods may vary in dimensions since greater support may be needed for an active athelete than for an older, sedentary person. To this end, a variety of screw clamp lengths may be provided for each of the forms described. The threaded end of the screw may be between 30 to 65 mm, and the screw threads may have a major diameter of between 5.4 mm and 6.9 mm or more, with a minor diameter of between 3.6 mm and 5.0 mm, with 9 threads per inch. The dimension from the flange to the end of the machine thread is usually the same for each clamp thus allowing for interchangeability of the saddle assemblies described as interchangeable to accommodate rods of different dimension. Maintaining the flange-to-end dimension also has the advantage of allowing replacement of only the shaft part of the screw assembly if that is necessary, i.e., use of a shaft with a longer threaded end in place of one with a shorter threaded end.

The rigid rods, for the dual or single rod system, may be from 4 to 8 inches in length and may be from 0.155 to 0.167 of an inch in diameter, with appropriate dimensions of the apertures to provide an interference fit, as described. If more strength is needed, the diameter of the rods may be increased since an increase in diameter of 0.020 of an inch tends to increase the rod strength by 50%. To illustrate the strength of the present system, the use of four rods of 0.155 of an inch diameter is thirty percent stronger than the use of 3/16 of an inch Luque rods.

As a general rule, rods of the same dimension are used on each side of the spinal column and in each set of clamps. It is understood, however, that there may be instances in which it may be desirable to provide a stronger support system on one side of the spinal column in which case the rods on one side may be of a greater diameter. It may also be desirable to provide more local support close to the center axis of the spine, in which event one of the rods affixed to the clamps may be of a greater diameter than the other rod affixed to the same clamp, the clamps being appropriately proportioned for purchase and interference fit with respect to each of the rods.

All implanted components of the support fixation are fabricated of AISI 316L stainless steel, a chromium-nickel-molybdenum alloy, and chemically polished and passivated to resist corrosion by the body fluids and tissue, rather than electropolishing the finished parts. Electropolishing may cause intergranular corrosion which tends to promote metal fatigue.

Another advantage of the present system is that the components are firmly purchased and thus provide stability of internal fixation in that there is no sliding or relative movement between the parts. Such sliding or relative movement between the components of an implanted system are objectionable since this may result in destruction of the passive layer and may lead to a repassivation process which leads to corrosion and metal fatigue.

It is apparent from the foregoing detailed description that the present invention has many advantages over the support systems and methods of the prior art, as heretofore set forth. It will also be apparent that various modifications may be made to the support fixation and methodology of this invention by those skilled in the art without departing from the scope of the appended claims.

We claim:

1. A screw clamp assembly for use in a spinal support fixation system for inhibiting front to back, side to side and rotational movements of a preselected portion of the spinal column comprising:
   a screw clamp shaft member having a threaded end portion adapted to be screwed into a preselected position of the vertebra of the spinal column,
   a saddle assembly mounted on said threaded end portion of said screw clamp shaft member and including mating half saddles which form at least one pair of spaced rod receiving apertures,
   said apertures being in opposed facing and spaced relationship and being dimensioned to receive at least one rod of a predetermined dimension to effect purchase securely on the rod assembled thereto, and
   means to secure the mating half saddles together such that the rod positioned in the rod securing apertures are gripped by said mating half saddles along a predetermined length of the surface of said rod to secure said rod firmly to said screw clamp assembly and in a predetermined orientation with respect to said spinal column.

2. A screw clamp assembly as set forth in claim 1 wherein said saddle assembly includes two pairs of said facing apertures in which one pair of each pair is located laterally on each side of said threaded end portion.

3. A screw clamp assembly as set forth in claim 1 wherein said facing apertures are serrated for gripping a serrated rod along a predetermined length.

4. A screw clamp assembly as set forth in claim 1 wherein said apertures are generally circular in cross-section and are dimensioned to form an interference fit with respect to the rods received therein.

5. A screw clamp assembly as set forth in claim 1 further including a flange on one end of threaded end portion to support said saddle assembly.

6. A screw clamp assembly as set forth in claim 1 in which one of said half saddles includes finger means which overhang the other mating half saddle.

7. A screw clamp assembly as set forth in claim 1 wherein said screw clamp shaft member includes a second threaded portion and at least one of said mating half saddles being received over said second threaded portion.

8. A screw clamp assembly as set forth in claim 1 wherein said mating half saddles include an upper and lower half saddle unit,
   said lower half saddle unit including an opening for reception on said screw clamp shaft member.

9. A screw clamp assembly as set forth in claim 8 wherein said opening in said lower half saddle unit is formed in a side face thereof so that said lower half saddle unit may be assembled laterally on said screw clamp shaft member.

10. A screw clamp assembly as set forth in claim 8 further including lock means to secure said lower half saddle unit against axial movement on said screw clamp shaft member.

11. A screw clamp assembly as set forth in claim 9 wherein said opening in said lower half saddle unit includes lock receiving means having spaced vertically extending walls, and
   lock means received in said lock receiving means for securing said lower half saddle unit on said screw clamp shaft member to prevent lateral movement thereof with respect to said screw clamp shaft member.

12. A screw clamp member as set forth in claim 11 wherein said lock receiving means includes vertically extending walls each having a reverse tapered wall portion, and
   said lock means is a T-shaped insert having tapered side walls to form a dove-tail lock with said reverse tapered wall portion.

13. A screw clamp assembly as set forth in claim 5 further including a shoulder on said screw clamp shaft member in spaced relation to said flange,
   said saddle assembly including a lower half saddle unit received between said flange and said shoulder.

14. A screw clamp assembly as set forth in claim 1 wherein said apertures are in spaced parallel relationship.

15. A screw clamp assembly as set forth in claim 1 in which each said half saddle inludes a single aperture located laterally of said threaded end portion.

16. A screw clamp assembly for use in a spinal support fixation system for inhibiting front to back, side to side and rotational movements of a preselected portion of the spinal column comprising,
   a shaft member being threaded at each end,
   a flange formed adjacent the threads of one end of said shaft,
   a shoulder provided on said shaft in spaced relation to said flange,
   a saddle assembly mounted on said shaft and on one side of said flange,
   said saddle assembly being removable from said shaft and including mating upper and a lower half saddle units having faces in opposed relation,
   said upper half saddle unit including spaced depending finger means thereon and being provided with an opening therein for passage over a threaded end of said shaft,
   said lower half saddle unit including an opening for assembly on said shaft between said shoulder and said flange,
   a lock member received by said lower half saddle unit and operative to prevent lateral movement of said lower half saddle unit with respect to said shaft,
   said finger means being proportioned such that said lock member is retained in said lower saddle unit by said finger means,
   the faces in said saddle units being provided with at least one aperture arranged in facing relation, and
   said apertures being dimensioned to receive rod means and to form an interference fit therewith to effect a gripping purchase with the rods.

17. A spinal support fixation system for maintaining selected predetermined adjacent vertebra in a predetermined orientation to inhibit front to back, side to side and rotational movements of the supported portion of the spinal column comprising:
   a plurality of sets of screw clamp assemblies,
   each set of said screw assemblies including at least two screw clamp members and adapted to be placed into a vertebra,
   rod means received by said screw clamp assemblies and cooperating therewith to form a rigid support structure on each side of the vertebra,
   said clamp members including a threaded end for insertion into a bony supporting portion of the vertebra and a saddle assembly for supporting said rod members in spaced relation to each other,
   said saddle assembly including at least one spaced aperture for receiving at least one of said rod members, and
   said apertures being proportioned with respect to the dimensions of said rods whereby said saddle assembly clamps along a predetermined surface of said rods to effect firm purchase between said clamp member and the rod received by said clamp member.

18. A spinal support fixation system as set forth in claim 17 wherein there are tw apertures and wherein said apertures are proportioned with respect to said rods to form an interference fit therewith.

19. A spinal support system as set forth in claim 17 wherein said saddle assembly includes separable half saddles which are each separately removable from said rods.

20. A spinal support system as set forth in claim 19 wherein said apertures are provided in said separable half saddles.

21. A spinal support system as set forth in claim 17 wherein the saddle assembly includes a single aperture for receiving said rod member,
   said rod member having a serrated outer surface, and
   said apertures having a serrated surface to mate with the serratiions on said rod member.

22. A method of providing a spinal support system for inhibiting front to back, side to side and rotational movement of a portion of the spinal column, comprising the steps of:
   inserting into a preselected portion of a vertebra at least one screw clamp member,
   each new clamp including a surface portion defining a reference surface having a defined contour arranged in a predetermined relation to the spinal column,
   forming a temporary master having a contour which replicates said defined contour,
   using said temporary master to form a master pattern having surface portions related to each other in essentially the same relation as the contour of the reference surface of said screw clamps, using said master pattern to form at least two rod members to replicate the defined contour, and assembling said rod members to said clamps.

23. The method as set forth in claim 22 wherein at least two screw clamp members are inserted into the vertebra.

24. The method as set forth in claim 23 in which the step of forming said temporary master includes the step of bending relatively soft rod members to replicate said defined contour.

25. The method as set forth in claim 24 wherein at least some of said screw clamp members are mounted through the pedicle of the vertebra.

* * * * *